United States Patent
Collis et al.

(10) Patent No.: US 6,649,620 B2
(45) Date of Patent: Nov. 18, 2003

(54) QUINOLINE AND QUINAZOLINE COMPOUNDS USEFUL IN THERAPY

(75) Inventors: Alan John Collis, Sandwich (GB); David Nathan Fox, New York, NY (US)

(73) Assignee: Pfizer Inc., New York, NY (US)

(*) Notice: Subject to any disclaimer, the term of this patent is extended or adjusted under 35 U.S.C. 154(b) by 0 days.

(21) Appl. No.: 10/252,852

(22) Filed: Sep. 23, 2002

(65) Prior Publication Data

US 2003/0045525 A1 Mar. 6, 2003

Related U.S. Application Data

(63) Continuation of application No. 09/591,195, filed on Jun. 9, 2000, now abandoned, which is a continuation of application No. 09/067,608, filed on Apr. 28, 1998, now abandoned.

(30) Foreign Application Priority Data

May 1, 1997 (GB) .............................. 9708917

(51) Int. Cl.[7] ................. C07D 239/94; C07D 239/95; C07D 403/04; A61K 31/517
(52) U.S. Cl. ................. 514/260; 514/228.2; 514/233.8; 514/211.08; 514/212.01; 514/217.06; 514/218; 514/259; 540/600; 540/575; 540/553; 544/293; 544/291; 544/116
(58) Field of Search ................. 544/293, 291, 544/116; 540/600, 575, 553; 514/233.8, 260, 217.06

(56) References Cited

FOREIGN PATENT DOCUMENTS

WO  WO89/05297  6/1989

*Primary Examiner*—John M. Ford
(74) *Attorney, Agent, or Firm*—Peter C. Richardson; Gregg C. Benson; Carl J. Goddard

(57) ABSTRACT

Compounds of formula I,

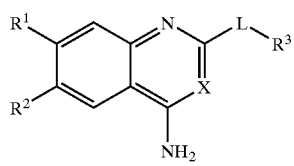

wherein
- $R^1$ represents $C_{1-4}$ alkoxy optionally substituted by one or more fluorine atoms;
- $R^2$ represents an aryl group or a heteroaryl group, optionally substituted by $C_{1-4}$ alkyl or $SO_2NH_2$;
- $R^3$ represents a 4-, 5-, 6-, or 7-membered heterocyclic ring containing at least one heteroatom selected from N, O and S, the ring being optionally fused to a benzene ring or a 5- or 6-membered heterocyclic ring containing at least one heteroatom selected from N, O and S, the ring system as a whole being optionally substituted;
- X represents CH or N; and
- L is absent, or represents a cyclic group of formula Ia,

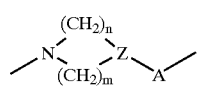

or represents a chain of formula Ib,

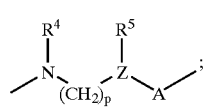

and pharmaceutically acceptable salts thereof, are useful in the treatment of a variety of disorders including benign prostatic hyperplasia.

8 Claims, No Drawings

QUINOLINE AND QUINAZOLINE COMPOUNDS USEFUL IN THERAPY

This application is a continuation of application Ser. No. 09/591,195, filed Jun. 9, 2000, now abandoned, which is a continuation of application Ser. No. 09/067,608, filed Apr. 28, 1998, now abandoned.

This invention relates to novel compounds useful in therapy, particularly in the treatment of benign prostatic hyperplasia.

International Patent Application WO 89/05297 discloses a number of substituted quinazoline compounds that are indicated as inhibitors of gastric acid secretion.

According to the present invention, there is provided a compound of formula I,

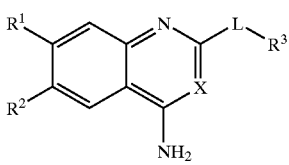

wherein
$R^1$ represents $C_{1-4}$ alkoxy optionally substituted by one or more fluorine atoms;
$R^2$ represents an aryl group or a heteroaryl group, optionally substituted by $C_{1-4}$ alkyl or $SO_2NH_2$;
$R^3$ represents a 4-, 5-, 6-, or 7-membered heterocyclic ring containing at least one heteroatom selected from N, O and S, the ring being optionally fused to a benzene ring or a 5- or 6-membered heterocyclic ring containing at least one heteroatom selected from N, O and S, the ring system as a whole being optionally substituted by one or more groups independently selected from OH, $C_{1-4}$ alkyl, $C_{1-4}$ alkoxy, halogen and $NHSO_2(C_{1-4}$ alkyl), and when S is a member of the ring system, it may be substituted by one or two oxygen atoms;
X represents CH or N; and
L is absent,
or represents a cyclic group of formula Ia,

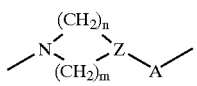

in which A is attached to $R^3$;
A represents CO or $SO_2$;
Z represents CH or N;
m represents 1 or 2, and in addition, when Z represents CH, it may represent 0; and
n represents 1, 2 or 3, provided that the sum of m and n is 2, 3, 4 or 5;
or represents a chain of formula Ib,

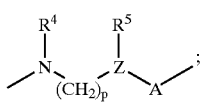

in which A is attached to $R^3$;
A and Z are as defined above;
$R^4$ and $R^5$ independently represent H or $C_{1-4}$ alkyl; and p represents 1, 2 or 3, and in addition, when Z represents CH, it may represent 0;
or a pharmaceutically acceptable salt thereof (referred to together herein as "the compounds of the invention").

Pharmaceutically acceptable salts include acid addition salts, such as hydrochloride and hydrobromide salts, and phosphate salts.

Alkyl or alkoxy groups that $R^{1-5}$ may represent or include can be straight chain, branched chain, cyclic, or a combination thereof.

"Aryl" in the definition of $R^2$ means an aromatic hydrocarbon, for example phenyl or naphthyl. "Heteroaryl" in the definition of $R^2$ means an aromatic heterocycle, for example one having 5 or 6 ring members, at least one of which is N, O or S, such as pyridinyl or furanyl.

Preferably, heterocyclic rings represented or comprised by $R^3$ are saturated. Examples include morpholine, thiomorpholine-1,1-dioxide, 1,4-dioxan, tetrahydrofuran and piperidine.

The compounds of the invention may be optically active. The invention includes all optical isomers of the compounds of formula I, and all diastereoisomers thereof.

The compounds of the invention may exist in a number of tautomeric forms. The invention includes all such tautomeric forms.

Preferred groups of compounds that may be mentioned include those in which:

(a) $R^1$ represents methoxy;
(b) $R^2$ represents phenyl or 2-pyridinyl;
(c) $R^3$ represents morpholinyl, or a piperidine ring which is fused to a benzene or pyridine ring;
(d) L is absent or represents 1,4-diazepanylcarbonyl

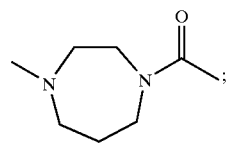

and (e) L is absent and $R^3$ represents a piperidine ring fused to a benzene ring which is substituted by $NHSO_2(C_{1-4}$ alkyl).

According to the invention, there is also provided a process for the production of a compound of the invention, which comprises:

(a) when X represents CH, cyclizing a compound of formula II,

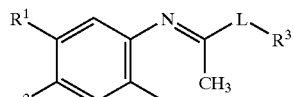

in which $R^{1-3}$ and L are as defined above;
(b) when Z represents N, reacting a compound of formula IIIa or IIIb, as appropriate.

IIIa

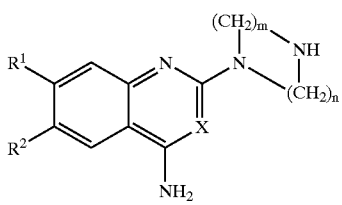

IIIb

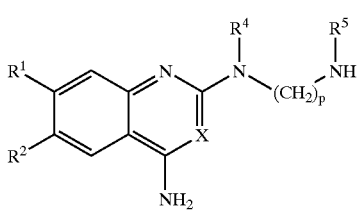

in which $R^1$, $R^2$, $R^4$, $R^5$, X, m, n and p are as defined above, with a compound of formula IV, Lg-A-$R^3$     IV in which $R^3$ is as defined above, A represents CO or $SO_2$ and Lg represents a leaving group;
(c) reacting a compound of formula V,

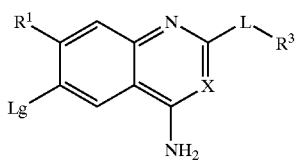

V in which $R^1$, $R^3$, X and L are as defined above, and Lg is a leaving group, with a compound of formula VI, $R^2$-M     VI in which $R^2$ is as defined above and M represents substituted boron, zinc or tin, in the presence of a palladium catalyst;
(d) when X represents N, reacting a compound of formula VII,

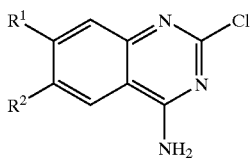

VII in which $R^1$ and $R^2$ are as defined above, with a compound of formula VIIIa, VIIIb or VIIIc, as appropriate,

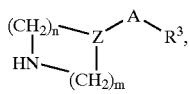

VIIIa

-continued

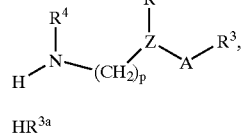

VIIIb $HR^{3a}$     VIIIc in which $R^{3-5}$, A, Z, m, n and p are as defined above; and $R^{3a}$ has the same significance as $R^3$ above except that it contains a nucleophilic nitrogen atom in the heterocyclic ring which is attached to the H in formula VIIIc;
(e) when A represents CO and $R^3$ comprises a nucleophilic nitrogen atom in the heterocyclic ring attached to L, reacting a compound of formula IXa or IXb, as appropriate.

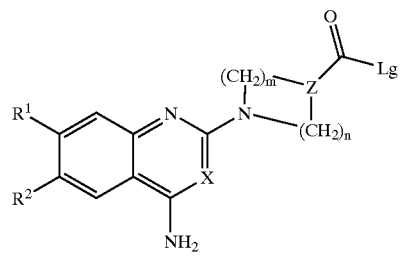

IXa

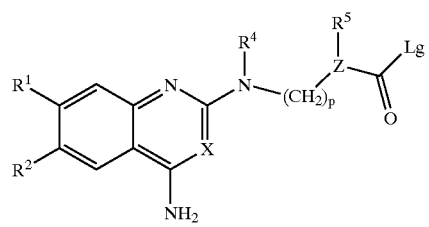

IXb in which $R^1$, $R^2$, $R^4$, $R^5$, X, Z, m, n and p are as defined above, and Lg is a leaving group, with a compound of formula VIIIc, as defined above; or
(f) conversion of a compound of formula I in which L represents a cyclic group of formula Ia, to a corresponding compound of formula I in which L represents a chain of formula Ib in which $R^4$ and $R^5$ each represent H, by the action of a strong base;
and where desired or necessary converting the resulting compound of formula I into a pharmaceutically acceptable salt or vice versa.

In process (a), the cyclization may be carried out in the presence of a strong base (for example lithium diisopropylamide) in a solvent that does not adversely affect the reaction (for example tetrahydrofuran), around room temperature. Alternatively, it may be performed using potassium hydroxide in a solvent which does not adversely affect the reaction (for example dimethylsulphoxide), at the reflux temperature of the solvent.

In process (b), suitable leaving groups are OH and Cl. When the compound of formula IV is a carboxylic acid, the reaction may be carried out in the presence of conventional coupling agents [for example 1-hydroxybenzotriazole monohydrate, 1-(3-dimethylaminopropyl)-3-ethylcarbodiimide hydrochloride and 4-methylmorpholine] in a solvent which does not adversely affect the reaction (for example $CH_2Cl_2$) at or around room temperature. When the leaving group is Cl, the reaction may be carried out in a solvent which does not adversely affect the reaction (for example CH$_2$Cl$_2$ or tetrahydrofuran), around 0° C. or up to the reflux temperature of the solvent.

In process (c), suitable leaving groups include the trifluoromethylsulphonate (triflate) group. The palladium catalyst may be tetrakis(triphenylphosphine)palladium(0). M may be B(OH)$_2$, B(CH$_2$CH$_2$)$_2$, Sn(CH$_2$CH$_2$CH$_2$CH$_3$)$_3$, Sn(CH$_3$)$_3$ or ZnCl. The reaction may be carried out in a solvent that does not adversely affect the reaction (for example, when M is B(OH)$_2$, a mixture of toluene, ethanol and 1M aqueous sodium carbonate) at an elevated temperature (for example the reflux temperature of the solvent).

In process (d), the reaction may be carried out in a solvent which does not adversely affect the reaction (for example n-butanol) in the presence of a base (for example triethylamine) at an elevated temperature (for example 100° C.).

In process (e), suitable leaving groups include Cl. The reaction may be carried out in a solvent that does not adversely affect the reaction (for example THF) in the presence of a base (for example triethylamine) at room temperature.

The reaction may also be carried out without isolating the compound of formula IXa or IXb, by reacting a compound of formula IIIa or IIIb with triphosgene and a compound of formula VIIIc. In this case the leaving group is —Cl. The reaction may be carried out in a solvent that does not adversely affect the reaction (for example CH$_2$Cl$_2$) in the presence of a base (for example triethylamine) at or around room temperature.

In process (f), suitable strong bases include lithium diisopropylamide. The reaction may be carried out in a solvent that does not adversely affect the reaction (for example THF).

Compounds of formula II [see process (a)] may be prepared by reaction of a compound of formula X,

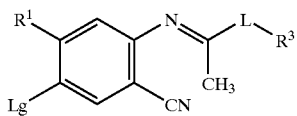

X in which R$^1$, R$^3$ and L are as defined above and Lg is a leaving group (such as a triflate group), with a compound of formula VI, as defined above, using the conditions described for process (c) above.

Compounds of formula X may be prepared by converting the OH group in a compound of formula XI.

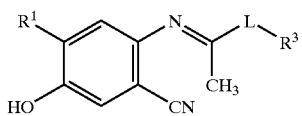

XI in which R$^1$, R$^3$ and L are as defined above, into a leaving group (such as a triflate), for example by reaction with triflic anhydride. The reaction may be carried out in a solvent which does not adversely affect the reaction (for example CH$_2$Cl$_2$) in the presence of pyridine, below room temperature (for example −20° C.).

Compounds of formula XI may be prepared by deprotecting a compound of formula XII,

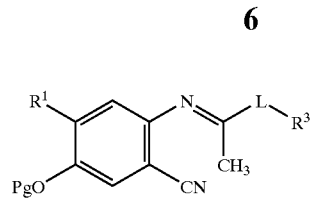

XII in which R$^1$, R$^3$ and L are as defined above and Pg is a hydroxy protecting group (such as benzyl). When Pg is benzyl, the deprotection may be achieved by hydrogenation over palladium-on-charcoal, in ethanol, around room temperature.

Compounds of formula XII may be prepared by reaction of a compound of formula XIII,

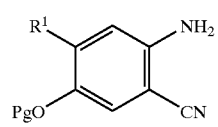

XIII in which R$^1$ and Pg are as defined above, with a combination of a compound of formula XIV,

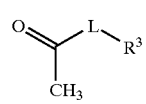

XIV in which R$^3$ and L are as defined above, and phosphorous oxychloride in dichloromethane at the reflux temperature of the solvent.

Compounds of formula IIIa or IIIb [see process (b)] in which X represents CH may be prepared from compounds of formula XVa or XVb, as appropriate,

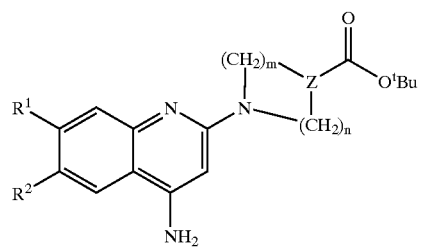

XVa

XVb in which R$^1$, R$^2$, R$^4$, R$^5$, m, n and p are as defined above, by bubbling HCl gas through a solution of the compound in dichloromethane.

Compounds of formula XVa or XVb may be prepared from compounds of formula XVIa or XVIb, as appropriate,

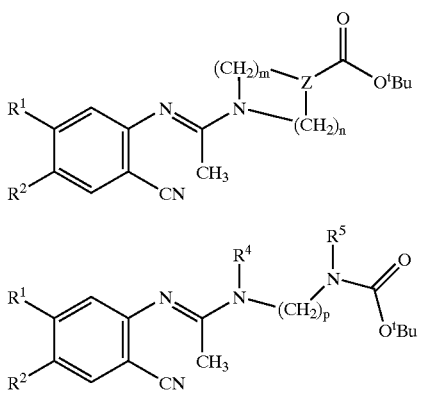

XVIa

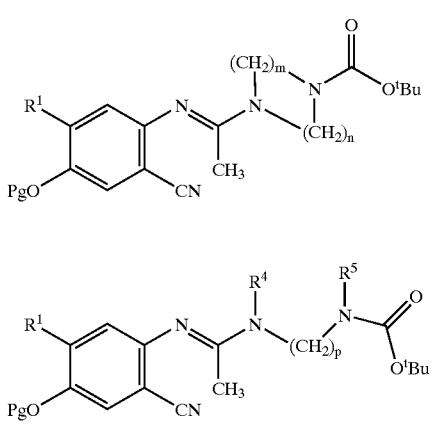

XVIb in which $R^1$, $R^2$, $R^4$, $R^5$, m, n and p are as defined above, by cyclization using potassium hydroxide or lithium diisopropylamide at an elevated temperature (such as 90° C.) in DMSO, quenching with water.

Compounds of formula XVIa or XVIb may be prepared from compounds of formula XVIIa or XVIIb, as appropriate, XVIIa XVIIb in which $R^1$, $R^4$, $R^5$, m, n and p are as defined above, and Pg is a hydroxy protecting group, by reaction with a compound of formula VI, as defined above, using the conditions described for process (c) above.

Compounds of formula XVIIa or XVIIb may be prepared by reacting a compound of formula XIII, as defined above, with a compound of formula XVIIIa or XVIIIb, as appropriate, XVIIIa

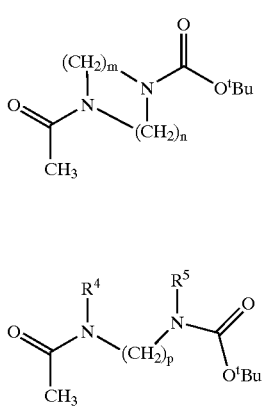

XVIIIb in which $R^4$, $R^5$, m, n and p are as defined above, by the method described above for producing compounds of formula XII.

Compounds of formula IIIa or IIIb [(see process (b)] in which X represents N may be prepared by reacting a compound of formula VII, as defined above, with a compound of formula XIXa or XIXb, as appropriate, XIXa

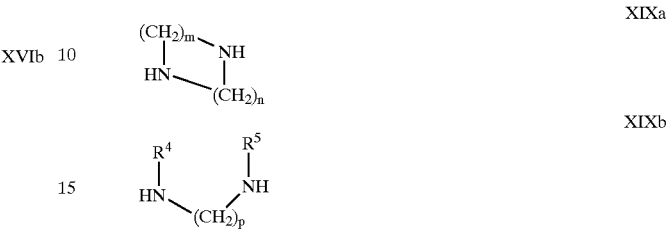

XIXb in which $R^4$, $R^5$, m, n and p are as defined above, using the conditions mentioned for process (d) above.

Compounds of formula VII may be prepared by conventional means from known compounds (or compounds available using known techniques) according to Scheme 1 below (see also Example 1), in which $R^1$, $R^2$ and M are as defined above:

Scheme 1

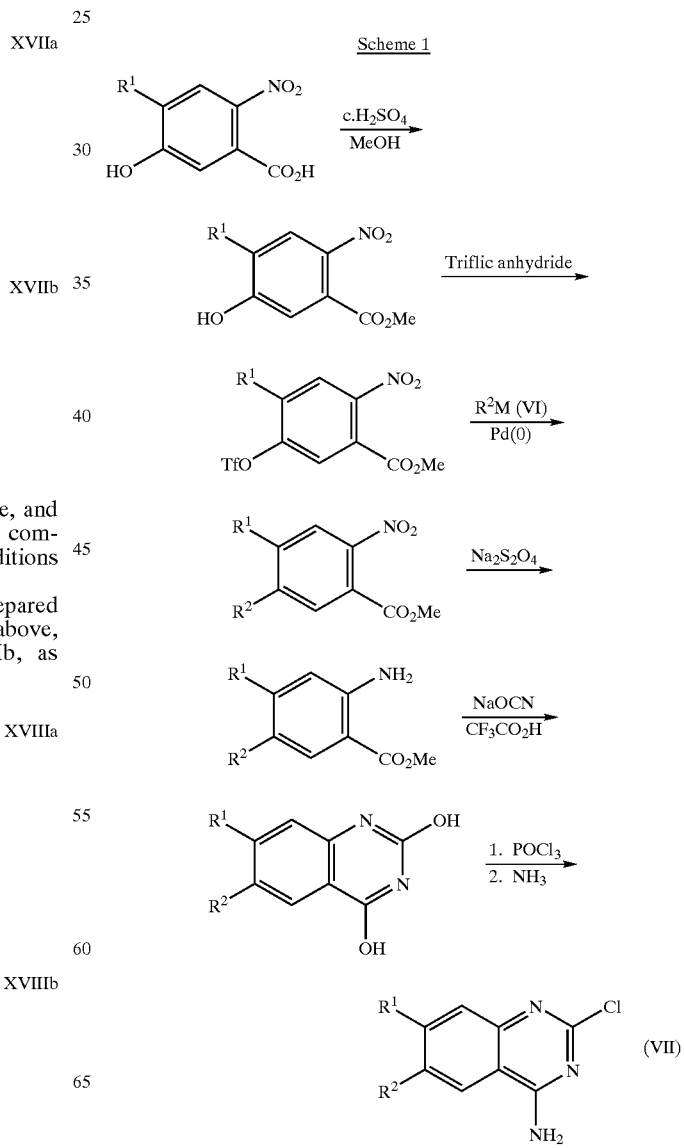

Compounds of formula V [see process (c)] in which X represents CH may be prepared by cyclization of a compound of formula X, as defined above, using the reaction conditions mentioned in process (a) above.

Compounds of formula V in which X represents N may be prepared by converting the OH group in a compound of formula XX,

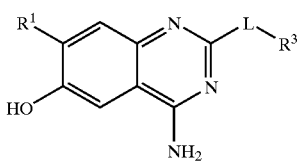

XX in which $R^1$, $R^3$ and L are as defined above, into a leaving group (such as a triflate group), for example by reaction with triflic anhydride.

Compounds of formula XX may be prepared from compounds of formula XXI,

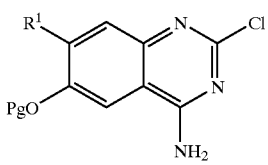

XXI in which $R^1$ and Pg are as defined above, by reaction with a compound of formula VIIIa, VIIIb or VIIIc, as defined above, as appropriate, using the conditions described in process (d).

Compounds of formula XXI may be prepared from compounds of formula XIII, as defined above, by conventional means according to Scheme 2 below (see also Example 11) in which $R^1$ and Pg are as defined above:

Scheme 2

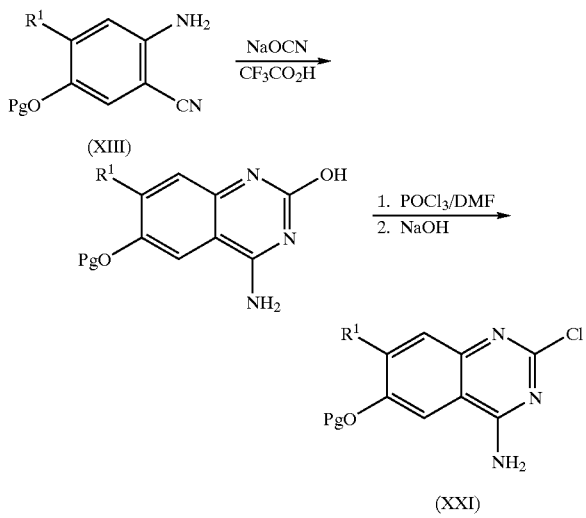

The preparation of compounds of formula VII [see process (d)] has already been described above.

Compounds of formula VIIIa and VIIIb may be prepared by reaction of a compound of formula IV, as defined above, with a compound of formula XIXa or XIXb, as defined above, as appropriate, using the conditions indicated for process (d) above.

Compounds of formula IXa and IXb [see process (e)] in which Lg represents Cl may be prepared from compounds of formula IIIa or IIIb, as defined above, as appropriate, by reaction with triphosgene. The reaction may be carried out in a solvent which does not adversely affect the reaction (for example $CH_2Cl_2$) in the presence of a base (for example triethylamine) at around $-10°$ C.

Compounds of formulae IV, VI, VIIIc, XIII, XIV, XVIIIa, XVIIIb, XIXa and XIXb are either known or are available using known techniques.

The intermediate compounds of formulae II, IIIa, IIIb, V, VII, IXa and IXb form a further aspect of the invention.

It will be apparent to those skilled in the art that sensitive functional groups may need to be protected and deprotected during synthesis of a compound of the invention. This may be achieved by conventional techniques, for example as described in 'Protective Groups in Organic Synthesis' by T W Greene and P G M Wuts, John Wiley and Sons Inc, 1991.

The compounds of the invention are useful because they possess pharmacological activity in animals. In particular, the compounds are useful in the treatment of a number of conditions including hypertension, myocardial infarction, male erectile dysfunction, hyperlipidaemia, cardiac arrhythmia and benign prostatic hyperplasia. The latter condition is of greatest interest. Thus, according to another aspect of the invention, there is provided a method of treatment of benign prostatic hyperplasia which comprises administering a therapeutically effective amount of a compound of the invention to a patient suffering from such a disorder. The use of the compounds of the invention as pharmaceuticals, and the use of the compounds of the invention in the manufacture of a medicament for the treatment of benign prostatic hyperplasia, are also provided.

The compounds of the invention may be administered by any convenient route, for example orally, parenterally (e.g. intravenously, transdermally) or rectally. The daily dose required will of course vary with the particular compound used, the particular condition being treated and with the severity of that condition. However, in general a total daily dose of from about 0.01 to 10 mg/kg of body weight, and preferably about 0.05 to 1 mg/kg, is suitable, administered from 1 to 4 times a day.

The compounds of the invention will generally be administered in the form of a suitable pharmaceutical formulation. Thus, according to another aspect of the invention, there is provided a pharmaceutical formulation including preferably less than 50% by weight of a compound of the invention in admixture with a pharmaceutically acceptable adjuvant, diluent or carrier. The pharmaceutical formulation is preferably in unit dose form. Such forms include solid dosage forms, for example tablets, pills, capsules, powders, granules, and suppositories for oral, parenteral or rectal administration; and liquid dosage forms, for example sterile parenteral solutions or suspensions, suitably flavoured syrups, flavoured emulsions with edible oils such as cottonseed oil, sesame oil, coconut oil and peanut oil, and elixirs and similar pharmaceutical vehicles.

Solid formulations may be prepared by mixing the active ingredient with pharmaceutical carriers, for example conventional tabletting ingredients such as corn starch, lactose, sucrose, sorbitol, talc, stearic acid, magnesium stearate, dicalcium phosphate, gums and other diluents, for example water, to form a homogeneous preformulation formulation in which the active ingredient is uniformly dispersed so that it may be readily subdivided into equally effective unit dosage forms containing typically from 0.1 to about 500 mg of the active ingredient. The solid dosage forms may be coated or otherwise compounded to prolong the action of the formulation.

The formulations of the invention may also contain a human 5-α reductase inhibitory compound [see International Patent Application WO 95/28397], or a compound of the invention could be presented in a pharmaceutical pack also containing a human 5-α reductase inhibitory compound as a combined preparation for simultaneous, separate or sequential use.

The compounds of the invention may be tested in the screens set out below.

Contractile Responses of Human Prostate

Prostatic tissue was cut into longitudinal strips (approximately 3×2×10 mm) and suspended in organ baths under a resting tension of 1 g in Krebs Ringer bicarbonate of the following composition (mM): NaCl (119), KCl (4.7), $CaCl_2$ (2.5), $KH_2PO_4$ (1.2), $MgSO_4$ (1.2), $NaHCO_3$ (25), glucose (11), and gassed with 95% $O_2$/5% $CO_2$. The solution also contained 10 mM cocaine and 10 mM corticosterone. Tissues were exposed to a sensitising dose of (−)-noradrenaline (100 mM) and washed over a 45 minute period. Isometric contractions were obtained in response to cumulative additions of (−)-noradrenaline to obtain control curves in all tissues. A further curve was then generated in the presence or absence of antagonist (incubated for 2 hours). Antagonist affinity estimates ($pA_2$) were determined using a single concentration of competing antagonist, $pA_2=-\log[A]/(DR-1)$ where the dose ratio (DR), relative to corresponding controls, was produced by a single concentration of antagonist [A], assuming competitive antagonism and Schild regression close to unity.

Anaesthetised Dog Model of Prostatic Pressure and Blood Pressure

Mature male beagles (12–15 kg body weight) were anaesthetised with sodium pentobarbitone (30–50 mg/kg i.v.) and a tracheal cannula was inserted. Subsequent anaesthesia was maintained using pentobarbitone infusion. The animals were respirated with air using a Bird Mk8 respirator (Bird Corp., Palm Springs, Calif. USA) adjusted to maintain blood gasses in the range $pO_2$ 90–110 mm Hg, $pCO_2$ 35–45 mm Hg, pH 7.35–7.45. Body temperature was maintained at 36–37.5° C. using a heated operating table. Catheters were placed into the left femoral artery for recording blood pressure and into the left femoral vein for compound administration. Heart rate was recorded via the lead II E.C.G. A laparotomy was performed to cannulate both ureters to prevent chance of fluid volume within the bladder. A 7F cardiac catheter (with a 1.5 ml capacity balloon tip) was inserted into the bladder via the urethra. The balloon was filled with air and the catheter withdrawn until the balloon became lodged in the prostate, which was confirmed by digital pressure. Balloon pressure was recorded via a Druck transducer. Prostatic pressure and haemodynamic parameters were made on a Grass Polygraph (Grass Instruments. Quincy, Mass, U.S.A.) and the data measured on line using a Motorola 68000-based microcomputer system (Motorola Inc., Temple, Ariz., U.S.A.). Compounds were made up in PEG 300 and administered i.v. through a catheter in the femoral vein. Responses to phenylephrine (1–16 μg/kg i.v. in saline) were obtained to generate control dose-response curves (two control curves for each experiment). Compounds were administered (in terms of compound base) at 10–300 μg/kg i.v. 5 min before construction of phenylephrine curves (constructed up to a maximum dose of 128 μg/kg in the presence of test compound).

Due to $α_1$-related dysrhythymic properties of phenylephrine, absolute maximal responses were not obtained but were taken as 10% greater than the control response obtained with 16 μg/kg phenylephrine. Drug concentrations were calculated on the basis of molar weight of compound/kg body weight thus allowing a "pseudo $pA_2$" calculation by Schild analysis using dose ratios derived from shifts in the phenylephrine dose-response curves.

The compounds of the invention may have the advantage that they are more potent, have a longer duration of action, have a broader range of activity, are more stable, have fewer side effects or are more selective (in particular they may have beneficial effects in benign prostatic hyperplasia without causing undesirable cardiovascular effects, for example because they are able to selectively antagonise prostatic receptor subtypes of the $α_1$-adrenoceptor), or have other more useful properties than the compounds of the prior art.

The invention is illustrated by the following examples, in which the following abbreviations are used:

DMF=dimethylformamide
DMSO=dimethylsulphoxide
EtOAc=ethyl acetate
EtOH=ethanol
h=hour
MeOH=methanol
min=minute
n-BuOH=n-butanol
THF=tetrahydrofuran Intermediate 1

1-(4-Morpholinecarbonyl)-1,4-diazepane hydrochloride (a) 1-(t-Butyloxycarbonyl)-1,4-diazepane To a solution of homopiperazine (100 g, 1.0 mol) and triethylamine (210 ml, 152 g, 1.5 mol) in $CH_2Cl_2$ (500 ml) at 0° C. was added a solution of di-(t-butyl) dicarbonate (195 g, 0.89 mol) in $CH_2Cl_2$ (300 ml). The mixture was allowed to warm to room temperature and stirred for 18 h after which time the $CH_2Cl_2$ was evaporated under reduced pressure. The resulting residue was partitioned between ether and 2N citric acid and the aqueous layer was extracted with ether (4×200 ml). The aqueous layer was basified with 2N aqueous NaOH and then extracted with $CH_2Cl_2$ (4×400 ml). The combined $CH_2Cl_2$ extracts were washed with $H_2O$ (2×), saturated brine (1×) and dried over $MgSO_4$. Evaporation under reduced pressure followed by azeotroping with $CH_2Cl_2$ (4×) gave the subtitle compound as a yellow waxy solid (94.3 g, 53%). $R_f$ 0.25 ($CH_2Cl_2$/MeOH/0.88 $NH_3$ 90/10/1, v/v). MS m/z 201 (MH$^+$). Found: C,58.86; H,10.03; N,13.58; $C_{10}H_{20}N_2O_2$ 0.05.$CH_2Cl_2$ requires C,59.02: H, 9.91; N,13.70%.

(b) 1-(t-Butyloxycarbonyl)-4-(4-morpholinecarbonyl)-1,4-diazepane

A solution of the compound of step (a) (92.0 g, 0.46 mol) and triethylamine (96.0 ml, 69.7 g. 0.69 mol) in $CH_2Cl_2$ (500 ml) at 0° C. was treated dropwise with a solution of 4-morpholinecarbonyl chloride (64.0 ml, 82.0 g, 0.55 mol) in $CH_2Cl_2$ (100 ml) and the reaction was stirred at room temperature under $N_2$ for 18 h. The reaction mixture was then diluted with $CH_2Cl_2$ (400 ml) and washed with 2N citric acid (3×400 ml), saturated brine (1×500 ml), dried over $MgSO_4$ and evaporated to give the subtitle compound as an off-white solid (141.7 g, 98%). $R_f$ 0.80 ($CH_2Cl_2$/MeOH/0.88 $NH_3$ 90/10/1, v/v). MS m/z 314 (MH$^-$). Found: C,57.50; H,8.69; N,13.41; $C_{15}H_{27}N_3O_4$ requires C,57.50; H,8.69; N,13.41%.

(c) 1-(4-Morpholinecarbonyl)-1,4-diazepane hydrochloride

A solution of the compound of step (b) (140.0 g, 0.44 mol) in $CH_2Cl_2$/MeOH (1/1, v/v, 600 ml) at 0° C. was saturated with HCl gas and the reaction mixture was stirred at room temperature under $N_2$ for 18 h after which time the reaction mixture was evaporated under reduced pressure and slurried in EtOAc to give, after filtration, a white hygroscopic solid. This was further purified by slurrying in acetone, filtering, washing with ether and drying under reduced pressure at 60° C. to give the title compound as a colourless solid (99.0 g, 90%). $R_f$ 0.41 ($CH_2Cl_2$/MeOH/0.88 $NH_3$ 84/14/2, v/v). MS m/z 214 (MH$^+$). Found: C,47.50; H,8.10; N,16.55; $C_{10}H_{19}N_3O_2$ HCl 0.2.$H_2O$ requires C,47.41; H,8.12; N,16.59%.

Intermediate 2
1-Acetyl-4-(4-morpholinecarbonyl)-1,4-diazepane

To a solution of Intermediate 1 (50 g, 0.2 mol) and triethylamine (42 ml, 30.5 g, 0.3 mol) in $CH_2Cl_2$ (400 ml) at 5° C. was added acetic anhydride (23 ml, 24.9 g, 0.24 mol) dropwise over 15 min and the reaction was then stirred for a further 2 h at room temperature under $N_2$. Dilution with $CH_2Cl_2$ (600 ml) was followed by washing with saturated aqueous sodium bicarbonate (2×200 ml) and the combined aqueous layers extracted with $CH_2Cl_2$ (1×100 ml). The $CH_2Cl_2$ layers were combined and washed with saturated brine, dried over $MgSO_4$ and evaporated to give a light brown oil. This was dissolved in $CH_2Cl_2$ (300 ml) and treated with triethylamine (8 ml, 5.8 g, 0.06 mol) and EtOH (5 ml), stirred for 1 h at room temperature then washed with saturated sodium bicarbonate and the aqueous layer extracted with $CH_2Cl_2$ (5×). The combined $CH_2Cl_2$ layers were dried over $MgSO_4$ and evaporated under reduced pressure to give a yellow oil that was then azeotroped with $CH_2Cl_2$ (4×) to give the title compound as a yellow oil (47.1 g, 92%). $R_f$ 0.45 ($CH_2Cl_2$/MeOH/0.88 $NH_3$ 90/10/1, v/v). MS m/z 256 (MH$^+$). Found: C,52.62; H,8.18; N,15.02; $C_{12}H_{21}N_3O_3$ 0.3.$CH_2Cl_2$ requires C,52.61; H,7.75; N,14.96%.

Intermediate 3
1-(4-Morpholinesulphonyl)-1,4-diazepane hydrochloride
(a) 1-(t-Butyloxycarbonyl)-4-{4-morpholinesulphonyl}-1,4-diazepane The subtitle compound was prepared by the method of Intermediate 1(b) from the compound of Intermediate 1(a) and 4-morpholinesulphonyl chloride [Repine et al, J. Med. Chem., 34, 1935 (1991)]. The reaction mixture was partitioned between $CH_2Cl_2$ and 1N NaOH. The organic phase was washed with 1N HCl, then $H_2O$ and dried over $MgSO_4$ and evaporated under reduced pressure. Purification on silica gel eluting with $CH_2Cl_2$/MeOH/0.88 $NH_3$ (98/1.25/0.25, v/v) initially and then (96/3.5.0.5, v/v) gave the subtitle compound as a gum (53%). $R_f$ 0.44 ($CH_2Cl_2$/MeOH/0.88 $NH_3$ 96/3.5/0.5, v/v). MS m/z 350 (MH$^+$). $^1$H NMR (CDCl$_3$) δ: 1.4 (9H, s), 1.9 (2H, m), 3.17 (4H, m), 3.22 (2H, m), 3.4 (2H, m), 3.5 (2H, m), 3.73 (6H, m).

(b) 1-(4-Morpholinesulphonyl)-1,4-diazepane hydrochloride

The title compound was prepared by the method of Intermediate 1(c) from the product of step (a) above. The subtitle compound (97%) was obtained as a white solid. $R_f$ 0.09 ($CH_2Cl_2$/MeOH/0.88 $NH_3$ 92/7/1, v/v). MS m/z 250 (MH$^+$). $^1$H NMR (d$_6$-DMSO) δ: 2.1 (2H, m), 3.1 (4H, m), 3.4 (4H, m), 3.62 (8H, m), 9.2 (2H, b).

Intermediate 4
2-Acetyl-5-methanesulfonamido-1,2,3,4-tetrahydroisoquinoline
(a) 5-Methanesulfonamidoisoquinoline Methanesulfonyl chloride (3.2 ml, 42 mmol) was added to a solution of 5-aminoisoquinoline (5.0 g, 35 mmol) in pyridine (40 ml) and the mixture was allowed to stand for 72 h. The reaction mixture was then poured into aqueous citric acid (10%, 400 ml) and extracted with EtOAc (2×230 ml). The organic layer was evaporated to give a residue that was purified on silica gel, eluting with $CH_2Cl_2$/MeOH, to afford the subtitle compound as a solid (3.55 g, 46%). $R_f$ 0.03 ($CH_2Cl_2$/ether 4/1, v/v). $^1$H NMR (D$_6$-DMSO) δ: 3.07 (3H, s), 7.68 (1H, t), 7.75 (1H, d), 8.03 (1H, d), 8.10 (1H, d), 8.54 (1H, d), 9.32 (1H, s), 9.79 (1H, bs).

(b) 5-Methanesulfonamido-1,2,3,4-tetrahydroisoquinoline hydrochloride

A solution of the product of step (a) (3.50 g, 15.7 mmol) in EtOH (250 ml) was treated with platinum dioxide (1.5 g) and 1N HCl (15.7 ml). The mixture was hydrogenated at a pressure of 414 kPa (60 psi) for 16 h, after which time the reaction mixture was filtered. The filtrate was evaporated under reduced pressure and triturated with $CH_2Cl_2$ to afford the subtitle compound as a colourless solid. The solid residue from the filtration was taken up into MeOH/$H_2O$ (1:2 v/v), and the suspension filtered, washing with $CH_2Cl_2$ (3×). This filtrate was evaporated to afford a second crop of the subtitle compound (total yield 3.45 g, 84%). $R_f$ 0.21 ($CH_2Cl_2$/MeOH/0.88 $NH_3$ 90/10/1, v/v). $^1$H NMR (D$_6$-DMSO) δ: 2.96–3.10 (2H, m). 3.31 (3H, m), 4.21 (2H, s), 7.12 (1H, m), 7.26 (2H, m), 9.24 (1H, s), 9.61 (2H, bs).

(c) 2-Acetyl-5-methanesulfonamido-1,2,3,4-tetrahydroisoquinoline

To a solution of the product of step (b) (2.87 g, 10.9 mmol) in $CH_2Cl_2$ at 0° C. was added acetic anhydride (1.2 ml, 13.1 mmol) and triethylamine (3.4 ml, 24.0 mmol), and the reaction was stirred at room temperature for 16 h. The reaction mixture was then partitioned between EtOAc and aqueous sodium bicarbonate solution and the aqueous phase extracted with further portions of EtOAc. The combined organic extracts were dried over $MgSO_4$ and evaporated to afford an oil. This was dissolved in MeOH (15 ml) and treated with aqueous sodium carbonate solution (7%, w/w, 15 ml) and the mixture stirred for 16 h at room temperature, after which time the MeOH was removed under reduced pressure, the pH was adjusted to pH 8 with 2N HCl and the product was extracted with EtOAc (2×). The combined organic extracts were dried over $MgSO_4$ and evaporated to give an oil that was purified on silica gel, eluting with $CH_2Cl_2$/MeOH (95/5, v/v) to give the title compound as an oil (2.0 g, 68%). $R_f$ 0.20 ($CH_2Cl_2$/MeOH 9/5, v/v). MS m/z 269 (MH$^+$).

EXAMPLE 1

4-Amino-7-methoxy-2-[4-(4-morpholinesulphonyl)-1,4-diazepan-1-yl]-6-phenylquinazoline hydrochloride (a) 5-Hydroxy-4-methoxy-2-nitrobenzoic acid, methyl ester To a solution of 5-hydroxy-4-methoxy-2-nitrobenzoic acid [Sinha J. Ind. Chem. Soc., 47, 925 (1970)] (83.0 g, 0.39 mol) in MeOH (250 ml) was added concentrated $H_2SO_4$ (20 ml) and the reaction mixture was heated to reflux for 16 h. On cooling, the reaction mixture was poured into aqueous potassium carbonate solution and acetic acid was added until pH 4 was reached. The mixture was extracted with chloroform, the organic layer washed twice with $H_2O$ and dried over $MgSO_4$. Evaporation under reduced pressure afforded the subtitle compound as yellow crystals (77.0 g, 87%). $R_f$ 0.30 (benzene/acetone 4/1, v/v); m.p. 146–9° C.

(b) 4-Methoxy-2-nitro-5-trifluoromethanesulfonatobenzoic acid, methyl ester

To a solution of the product of step (a) (30.0 g, 0.13 mol) in $CH_2Cl_2$ (1.31) was added pyridine (32.0 ml, 0.40 mol) and the mixture stirred at room temperature for 66 h, after which time it was cooled to −20° C. and triflic anhydride (32.5 ml, 0.20 mol) was added dropwise. The reaction mixture was allowed to warm to room temperature over 3 h and then stirred for a further 3 h. After this, H$_2$O (500 ml) was added, the organic layer was separated, dried over MgSO$_4$ and evaporated under reduced pressure to afford a yellow oil. This was passed through a pad of silica gel, washing with CH$_2$Cl$_2$, and evaporated to afford a yellow solid which on recrystallisation with Et$_2$O afforded the subtitle compound as a colourless solid (39.6 g, 85%). R$_f$ 0.50 (CH$_2$Cl$_2$/MeOH 95/5, v/v). MS m/z 377 (MNH$_4^+$)

(c) 4-Methoxy-2-nitro-5-phenylbenzoic acid, methyl ester

A solution of the product of step (b) (15.0 g, 40 mmol) in toluene (200 ml) and EtOH (100 ml) was treated with phenylboronic acid (6.1 g, 50 mmol), tetrakis (triphenylphosphine)palladium (2.4 g, 2 mmol) and 2N aqueous sodium carbonate (45 ml) and the mixture was heated to reflux for 1 h. The mixture was then cooled and partitioned between EtOAc and H$_2$O. The organic layer was separated, dried over MgSO$_4$, evaporated under reduced pressure and then passed through a plug of silica gel, washing with CH$_2$Cl$_2$, evaporated under reduced pressure and the solid purified by trituration with hexane. This afforded the subtitle compound as an off-white solid (11.4 g, 99%). R$_f$ 0.48 (CH$_2$Cl$_2$). MS m/z 305 (MNH$_4^+$).

(d) 2-Amino-4-methoxy-5-phenylbenzoic acid, methyl ester

To a solution of the product of step (c) (12.19 g, 43 mmol) in CH$_2$Cl$_2$ (200 ml) was added tetra-n-butylammonium chloride (7.1 g, 26 mmol) followed by a suspension of sodium dithionite monohydrate (81.6 g, 430 mmol) in H$_2$O (250 ml) and the resulting mixture was stirred rapidly for 30 min at room temperature. A further portion of sodium dithionite monohydrate (40.8 g, 215 mmol) in H$_2$O (150 ml) was added and stirring continued for a further 30 min at room temperature. The mixture was then basified with 2N aqueous NaOH, the organic layer separated, dried over MgSO$_4$ and concentrated to 100 ml under reduced pressure. Treatment with excess ethereal HCl was followed by neutralisation with 2N aqueous NaOH and the organic layer was separated, dried over MgSO$_4$ and evaporated under reduced pressure to give a green oil. Purification on silica gel, eluting with EtOAc afforded the subtitle compound as a yellow oil (10.76 g, 99%). R$_f$ 0.79 (CH$_2$Cl$_2$/MeOH 95/5, v/v). MS m/z 258 (MH$^+$).

(e) 7-Methoxy-6-phenylquinazoline-2,4-dione

To a solution of the product of step (d) (10.75 g, 41.8 mmol) in CH$_2$Cl$_2$ (200 ml) was added sodium cyanate (10.88 g, 167 mmol) followed by trifluoroacetic acid (13.3 ml, 167 mmol) and the reaction was stirred for 18 h at room temperature. The mixture was then partitioned between CH$_2$Cl$_2$ and H$_2$O, the organic layer was separated, dried over MgSO$_4$ and evaporated under reduced pressure to afford a yellow solid. This was suspended in aqueous NaOH (16.7 g in 150 ml H$_2$O) and warmed to 70° C. for 1 h after which time the mixture was cooled, acidified with concentrated HCl, and the resulting solid filtered and washed sequentially with water and acetone. This afforded the subtitle compound as an off-white solid (10.16 g, 91%). R$_f$ 0.16 (CH$_2$Cl$_2$/MeOH 95/5, v/v). $^1$H NMR (D$_6$-DMSO) δ: 3.85 (3H, s), 7.35 (2H, m), 7.45 (3H, m), 7.70 (1H, s), 7.75 (1H, s), 11.10 (2H, bd).

(f) 4-Amino-2-chloro-7-methoxy-6-phenylquinazoline

The product of step (e) (10.15 g, 40 mmol) was combined with phosphorus oxychloride (52.8 ml, 570 mmol) and N,N-dimethylaniline (12.0 ml, 90 mmol) and the mixture was heated to reflux for 1.5 h. The reaction mixture was then evaporated under reduced pressure, azeotroping with toluene (2×), and the resulting solid was partitioned between EtOAc and H$_2$O. The organic layer was separated and dried over MgSO$_4$, then passed through a plug of silica gel, washing with EtOAc, and evaporated to afford a yellow solid. This was dissolved in CH$_2$Cl$_2$ and treated with saturated methanolic NH$_3$ (150 ml) and the reaction stirred for 48 h at room temperature. Evaporation followed by suspension in MeOH and filtration, washing with ether, afforded the subtitle compound as a white solid (5.94 g, 55%). R$_f$ 0.57 (CH$_2$Cl$_2$/MeOH 95/5, v/v). MS m/z 286 (MH$^+$).

(g) 4-Amino-7-methoxy-2-[4-(4-morpholinesulphonyl)-1,4-diazepan-1-yl]-6-phenylquinazoline hydrochloride To a solution of the product of step (f) (300 mg, 1.05 mmol) and Intermediate 3 (300 mg, 1.05 mmol) in n-BuOH (5 ml) was added triethylamine (0.31 ml, 2.2 mmol), and the mixture was heated at 100° C. for 18 h. After cooling, the reaction mixture was evaporated under reduced pressure, partitioned between CH$_2$Cl$_2$ and saturated aqueous NaHCO$_3$. The organic layer was separated and dried over MgSO$_4$ to afford a brown solid. Trituration in hot isopropanol afforded the title compound as a colourless solid (86 mg, 16%). R$_f$ 0.22 (CH$_2$Cl$_2$/MeOH 95/5, v/v). MS m/z 499 (MH). $^1$H NMR (D$_6$-DMSO) δ: 1.90 (2H, m), 3.00 (4H, m), 3.45 (2H, m), 3.60 (6H, m), 3.90 (3H, s), 3.94 (2H, m), 4.00 (2H, m), 7.35–7.55 (5H, m), 7.65 (1H, bs), 8.20 (1H, s), 8.73 (1H, bs), 8.89 (1H, bs), 12.10 (1H, bs). Found: C,52.42; H,5.96; N,14.39. C$_{24}$H$_{31}$N$_6$O$_4$SCl H$_2$O 0.3.isopropanol 0.5.EtOAc 0.5.H$_2$O requires C,52.37; H,6.25; N,14.72%.

EXAMPLE 2

4-Amino-7-methoxy-6-phenyl-2-[4-(thiomorpholine-1,1-dioxide-4-carbonyl)-1,4-diazepan-1-yl] quinazoline hydrochloride (a) Thiomorpholine-1,1-dioxide hydrochloride 2-Chloroethyl chloroformate (0.72 ml, 6.7 mmol) was added dropwise to a solution of 4-methylthiomorpholine-1,1-dioxide (1.0 g, 6.7 mmol) in toluene (10 ml) at 0° C. under N$_2$. After 10 min, the reaction was warmed and maintained at reflux for 2 h. On cooling, the reaction mixture was evaporated and partitioned between EtOAc and H$_2$O. The organic layer was separated and washed sequentially with dilute HCl and saturated brine, then dried over Na$_2$SO$_4$ and evaporated. The residue was taken up in MeOH (10 ml) and heated at reflux for 2 h, after which time the mixture was evaporated and triturated with EtOAc to afford the subtitle compound (415 mg, 36%) as a solid. R$_f$ 0.34 (CH$_2$Cl$_2$/MeOH/0.88 NH$_3$ 90/10/1, v/v/v). MS m/z 136 (MH$^+$).

(b) Thiomorpholine-1,1-dioxide-4-carbonyl chloride

A solution of the product of step (a) (170 mg. 1.0 mmol) in CH$_2$Cl$_2$ (20 ml) at −20° C. was treated-sequentially with N,N-diisopropylethylamine (0.23 ml, 1.32 mmol) and triphosgene (90 mg, 0.31 mmol) and the reaction mixture stirred under N$_2$ for 1 h at room temperature. Evaporation under reduced pressure afforded the crude subtitle compound (207 mg. quantitative) which was used without further purification. R$_f$ 0.76 (CH$_2$Cl$_2$/MeOH/0.88 NH$_3$ 90/10/1, v/v).

(c) 4-Amino-7-methoxy-6-phenyl-2-[4-(thiomorpholine-1,1-dioxide-4-carbonyl)1,4-diazepan-1-yl]quinazoline hydrochloride To a solution of the compound of Example 1(f) (300 mg, 1.05 mmol) in n-BuOH (20 ml) was added homopiperazine (1.05 g, 10.5 mmol) and the mixture was heated to 100° C. for 5 h. After this, the reaction mixture was evaporated under reduced pressure and the residue partitioned between CH$_2$Cl$_2$ and 2N aqueous NaOH. The organic layer was separated, dried over MgSO$_4$ and evaporated to afford a foam. This was taken up in THF (20 ml), triethylamine (0.15 ml, 1.1 mmol) was added, followed by the product of step (b) (207 mg, 1.0 mmol), and the mixture was heated at reflux for 3 h. After cooling, the reaction mixture was evaporated under reduced pressure and partitioned between CH$_2$Cl$_2$ and 2N aqueous NaOH. The organic layer was separated, dried over MgSO$_4$ and evaporated under reduced pressure. The product was purified by chromatography on silica gel, eluting with CH$_2$Cl$_2$/MeOH (97/3, v/v) and then converted to the hydrochloride salt by treatment with excess ethereal HCl. This afforded the title compound as a colourless solid (130 mg, 23%). R$_f$ 0.76 (CH$_2$Cl$_2$/MeOH/0.88 NH$_3$ 84/14/2, v/v). MS m/z 511 (MH$^+$). $^1$H NMR (D$_6$-DMSO) δ: 1.94 (2H, m), 3.06 (4H, m), 3.34 (6H, m), 3.65 (2H, m), 3.86 (5H, m), 4.01 (2H, bm), 7.30–7.55 (5H, m), 7.80 (1H, bm), 8.19 (1H, s), 8.70 (1H, bs), 8.87 (1H, bs), 12.15 (1H, bs). Found: C,51.63; H,5.99; N,14.25. C$_{25}$H$_{31}$N$_6$O$_4$SCl 2.H$_2$O requires C,51.50; H,6.05; N,14.41%.

EXAMPLE 3

4-Amino-2-[4-(1,4-benzodioxan-2-carbonyl)-1,4-piperazin-1-yl]-7-methoxy-6-phenylquinazoline Prepared by a method analogous to Example 1(g) from the compound of Example 1(f) and 1-(1,4-benzodioxan-2-ylcarbonyl)piperazine [Campbell et al. J. Med. Chem., 30, 49 (1987)]. MS m/z 498 (MH$^+$)

EXAMPLE 4

(R/S)-4-Amino-7-methoxy-6-phenyl-2-[4-(tetrahydrofuran-2-carbonylamino)-1-propaneamino] quinazoline (a) 4-Amino-7-methoxy-6-phenyl-2-[N-(1,3-diaminopropyl)]quinazoline To a solution of the compound of Example 1(f) (1.0 g, 3.50 mmol) in n-BuOH (15 ml) was added 1,3-diaminopropane (2.9 ml, 35.0 mmol) and potassium iodide (5 mg) and the reaction mixture was heated to 100° C. for 18 h. After cooling, the reaction mixture was concentrated under reduced pressure, the residue suspended in CH$_2$Cl$_2$ and isolated by filtration. The solid was partitioned between EtOAc and 2N NaOH, the organic layer dried over MgSO$_4$ and evaporated under reduced pressure to afford the subtitle compound as a colourless foam (613 mg, 54%). R$_f$ 0.07 (CH$_2$Cl$_2$/MeOH/0.88 NH$_3$ 84/14/2, v/v). MS m/z 324 (MH$^+$).

(b) (R/S)-4-Amino-7-methoxy-6-phenyl-2-[4-(tetrahydrofuran-2-carbonylamino)-1-propaneamino] quinazoline To a solution of the product of step (a) (250 mg, 0.77 mmol) in CH$_2$Cl$_2$ was added (R/S)-tetrahydrofuran-2-carboxylic acid (99 mg, 0.85 mg), 1-hydroxybenzotriazole hydrate (157 mg, 1.16 mmol), 1-[3-dimethylaminopropyl]-3-ethylcarbodiimide hydrochloride (223 mg, 1.16 mmol) and triethylamine (0.16 ml, 1.16 mmol) and the reaction was stirred at room temperature under N$_2$ for 18 h. The reaction mixture was partitioned between CH$_2$Cl$_2$ and 2N NaOH, the organic layer was separated, dried over MgSO$_4$, and evaporated under reduced pressure to afford a colourless solid. This was recrystallised in EtOAc to afford the title compound as a colourless solid (143 mg, 44%). R$_f$ 0.58 (CH$_2$Cl$_2$/MeOH/0.88 NH$_3$ 84/14/2, v/v). MS m/z 422 (MH$^-$). $^1$H NMR (D$_6$-DMSO) δ: 1.62 (2H, m), 1.82 (2H, m), 1.90 (1H, m), 2.05 (1H, m), 3.04 (1H, m), 3.20–3.45 (5H, m), 3.75–3.84 (1H, m), 3.80 (3H, s), 4.23 (1H, m), 6.50 (1H, bs), 6.88 (1H, s), 7.20 (1H, bs), 7.30 (1H, m), 7.40 (2H, m), 7.50 (2H, m), 7.93 (1H, s), 8.04 (1H, bs). Found: C,64.11; H,6.50; N,15.87. C$_{23}$H$_{27}$N$_5$O$_3$ 0.6.H$_2$O requires C,63.90; H,6.58; N,16.20%.

EXAMPLE 5

(R/S)-4-Amino-7-methoxy-6-phenyl-2-[4-(tetrahydrofuran-2-carbonylamino)-1-N-methylpropaneamino]quinazoline The title compound was prepared from the compound of Example 1(f) by the method of Example 4, but using N-methyl-1,3-propanediamine in place of 1,3-diaminopropane. MS m/z 436 (MH$^+$).

EXAMPLE 6

4-Amino-7-methoxy-6-phenyl-2-[4-(4-morpholinecarbonyl-N-methylamino)propaneamino] quinazoline The title compound was prepared by the method of Example 4(a) from the compound of Example 1(f) and N-methyl-1,3-propanediamine, followed by reaction with 4-morpholinecarbonyl chloride using the method of Intermediate 1(b). MS m/z 498 (MH$^+$).

EXAMPLE 7

4-Amino-7-methoxy-6-phenyl-2-[4-(tetrahydrofuran-2-carbonyl)-1,4-piperazin-1-yl] quinazoline The title compound was prepared by the method of Example 4 from the compound of Example 1(f), but using piperazine in place of 1,3-diaminopropane. MS m/z 434 (MH$^+$).

EXAMPLE 8

4-Amino-7-methoxy-2-[4-(morpholinecarbonylamino)-1-propaneamino]-6-phenylquinazoline The compound of Example 4(a) was reacted with 4-morpholinecarbonyl chloride using the method of Intermediate 1(b) to give the title compound. MS m/z 437 (MH$^-$).

EXAMPLE 9

4-Amino-7-methoxy-2-[4-(morpholinecarbonylamino)-1-N-methylpropaneamino]-6-phenylquinazoline The title compound was prepared from the compound of Example 1(f) by the method of Example 4(a), but using N-methyl-1,3-propanediamine in place of 1,3-diaminopropane, followed by reaction with 4-morpholinecarbonyl chloride using the method of Intermediate 1(b). MS m/z 451 (MH$^+$)

EXAMPLE 10

4-Amino-7-methoxy-6-phenyl-2-(5,6,7,8-tetrahydro-1,6-naphthyrid-6-yl)quinazoline The title compound was prepared by the method of Example 1(g) from the compound of Example 1(f) and 5,6,7,8-tetrahydro-1,6-naphthyridine [Shiozawa et al. Chem. Pharm. Bull., 32, 2522 (1984)]. MS m/z 384 (MH$^-$).

EXAMPLE 11

2-Amino-7-methoxy-2-[4-(4-morpholinecarbonyl)-1,4-diazepan-1-yl]-6-phenylquinazoline (a) 3-Benzyloxy-4-methoxybenzonitrile 3-Benzyloxy-4-methoxybenzaldehyde (50 g, 0.21 mol) was added to a solution of sodium acetate (33.9 g, 0.41 mol) and hydroxylamine hydrochloride (28.73 g, 0.41 mol) in acetic acid (200 ml) and the resulting suspension was heated to reflux for 18 h. After cooling, the reaction mixture was partitioned between CH$_2$Cl$_2$ and H$_2$O and the aqueous phase was further extracted with CH$_2$Cl$_2$. The combined organic layers were dried over MgSO$_4$ and evaporated to afford the subtitle compound as a buff-coloured solid (43.9 g, 89%). R$_f$ 0.70 (toluene/EtOAc 4/1, v/v).

(b) 5-Benzyloxy-4-methoxy-2-nitro-benzonitrile

A solution of the product of step (a) (43.8 g. 0.18 mol) in glacial acetic acid (87 ml) was added dropwise to concentrated nitric acid (70% w/w, 244 ml) with periodic cooling to maintain the reaction temperature below 30° C. Once the addition was complete, the reaction was stirred for a further 30 min, after which time the mixture was poured into H$_2$O (1 l) and stirred for 30 min. The resulting precipitate was isolated by filtration, washed with H$_2$O and dried under reduced pressure at 50° C. to afford the subtitle compound as a white solid (35.1 g, 68%). R$_f$ 0.70 (EtOAc/hexane 1/1, v/v).

(c) 2-Amino-5-benzyloxy-4-methoxybenzonitrile

To a solution of the product of step (b) (35.0 g, 0.12 mol) in CH$_2$Cl$_2$ (500 ml) was added tetra-n-butylammnonium chloride (20.3 g, 0.074 mol) followed by a solution of sodium dithionite hydrate (118.0 g, 0.61 mol) in H$_2$O (400 ml) and the mixture was stirred vigorously for 2 h at room temperature. A further quantity of sodium dithionite hydrate (47.2 g) was then added and stirring continued for 1 h. The reaction mixture was then basified with 2N aqueous NaOH and the phases separated. The aqueous layer was extracted twice more with CH$_2$Cl$_2$ and the combined organic layers dried over MgSO$_4$ and concentrated under reduced pressure to a volume of 60 ml. Treatment with excess ethereal HCl led to the precipitation of an orange solid that was washed with ether and then dissolved in a mixture of CH$_2$Cl$_2$ and 2N aqueous NaOH. The phases were separated and the organic layer concentrated under reduced pressure and then dissolved in EtOAc and passed through a 5 cm plug of silica gel, eluting with EtOAc. On evaporation and drying under reduced pressure, the subtitle compound was obtained as a yellow solid (26.7 g, 85%). R$_f$ 0.76 (CH$_2$Cl$_2$/MeOH/0.88 NH$_3$ 90/10/1, v/v). MS m/z 255 (MH$^+$).

(d) 4-Amino-6-benzyloxy-2-hydroxy-7-methoxyquinazoline

A solution of the product of step (c) (26.7 g, 0.10 mol) in CH$_2$Cl$_2$ was treated with sodium cyanate (17.1 g, 0.26 mol) and trifluoroacetic acid (20.9 ml, 0.26 mol) was added dropwise to the resulting mixture at room temperature. After 45 min, the mixture was diluted with CH$_2$Cl$_2$ (1 l) and stirred for a further 18 h. The mixture was then concentrated under reduced pressure and partitioned between MeOH and 2N aqueous NaOH and stirred for 2 h. The MeOH was then removed under reduced pressure and the yellow solid isolated by filtration, washing sequentially with H$_2$O, acetone and ether to afford the subtitle compound as a yellow solid (18.0 g, 54%). A further quantity of product was obtained by concentration of the filtrate, acidification with concentrated HCl (95 ml), warming on a steam bath for 5 min, cooling and neutralisation with solid potassium carbonate. The solid obtained was isolated by filtration, washing sequentially with H$_2$O, EtOH and ether to afford the subtitle compound as a yellow solid (12.11 g, 93% combined yield). R$_f$ 0.23 (CH$_2$Cl$_2$/MeOH/0.88 NH$_3$ 84/14/2, v/v). MS m/z 298 (MH$_+$).

(e) 4-Amino-6-benzyloxy-2-chloro-7-methoxyquinazoline

DMF (7.9 ml, 0.10 mol) was added dropwise to phosphorus oxychloride (47.9 ml, 0.52 mol) with stirring. After 10 min, the product of step (d) (16.4 g, 0.055 mol) was added portionwise and the resulting mixture heated at 90° C. for 1.5 h, then cooled and poured into EtOAc (750 ml). The mixture was neutralised by the portionwise addition of aqueous sodium carbonate and the phases were separated. The organic layer was evaporated to dryness and the residue combined with the organic phase that was then treated with aqueous NaOH to basify (pH 10) and the mixture was heated at 90° C. for 2 h. After cooling, the mixture was partitioned between CH$_2$Cl$_2$ (1 l) and H$_2$O (1 l), the organic phase washed with H$_2$O, dried over MgSO$_4$ and evaporated to give a pale yellow solid. Trituration with isopropanol afforded the subtitle compound as a colourless solid (4.64 g, 27%). R$_f$ 0.64 (EtOAc/MeOH 95/5, v/v). MS m/z 316, 318 (MH$^+$).

(f) 2-Amino-6-benzyloxy-7-methoxy-2-[4-(4-morpholinecarbonyl)-1,4-diazepan-1-yl]quinazoline The subtitle compound was prepared by the method of Example 1(g) from the product of step (e) and Intermediate 1. The product was purified on silica gel eluting with EtOAc/MeOH (9/1, v/v) to afford the subtitle compound (46%) as a foam. R$_f$ 0.67 (CH$_2$Cl$_2$/MeOH/0.88 NH$_3$ 84/14/2, v/v). MS m/z 493 (MH$^-$).

(g) 2-Amino-6-hydroxy-7-methoxy-2-[4-(4-morpholinecarbonyl)-1,4-diazepan-1-yl]quinazoline The product of step (f) (360 mg, 0.73 mmol) was dissolved in EtOH (60 ml), 10% palladium on charcoal (100 mg, 0.09 mmol) was added and the reaction mixture hydrogenated at room temperature at a pressure of 414 kPa (60 psi) for 18 h. The reaction mixture was filtered and concentrated under reduced pressure and the residue purified on silica gel, eluting with CH$_2$Cl$_2$/MeOH/0.88 NH$_3$ (92/7/1, v/v) to afford the subtitle compound as foam (135 mg. 47%). R$_f$ 0.33 (CH$_2$Cl$_2$/MeOH/0.88 NH$_3$ 84/14/2. v/v). MS m/z 403 (MH$^-$).

(h) 2-Amino-7-methoxy-2-[4-(4-morpholinecarbonyl)-1,4-diazepan-1-yl]-6-trifluoromethylsulfonatoquinazoline To a solution of the product of step (g) (3.3 g, 8.2 mmol) in CH$_2$Cl$_2$ (80 ml), pyridine (2.0 ml, 25 mmol) was added. The solution was cooled to –20° C. and triflic anhydride (2.0 ml, 12.3 mmol) was added dropwise. The reaction mixture was allowed to warm to room temperature and stirred for a further 18 h, after which time it was partitioned between CH$_2$Cl, and H$_2$O, the solid residue dissolved in EtOAc and the organic layers combined, washed with water, dried over MgSO$_4$ and evaporated under reduced pressure. The product was purified by chromatography on silica gel, eluting with CH$_2$Cl$_2$/MeOH/0.88 NH$_3$ (96/3.5/0.5, v/v) to afford the subtitle compound as a colourless solid (2.5 g, 57%). R$_f$ 0.36 (CH$_2$Cl$_2$/MeOH/0.88 NH$_3$ 92/7/1, v/v). MS m/z 535 (MH$^+$).

(i) 2-Amino-7-methoxy-2-[4-(4-morpholinecarbonyl)-1,4-diazepan-1-yl]-6-phenylquinazoline To a solution of the product of step (h) (200 mg, 0.37 mmol) in dioxan (5 ml) was added trimethylphenylstannane (0.71 ml, 0.37 mmol), lithium chloride (48 mg, 1.11 mmol) and tetrakis(triphenylphosphine)palladium (9 mg, 0.007 mmol) and the reaction mixture heated to reflux for 18 h under N$_2$. After cooling and evaporation under reduced pressure, the residue was dissolved in CH$_2$Cl$_2$, filtered through a pad of Hyflo® diatomaceous earth and evaporated under reduced pressure. The product was purified by chromatography on silica gel, eluting with CH$_2$Cl$_2$/MeOH (95/5, v/v) to afford the title compound as a colourless foam (65 mg, 38%). R$_f$ 0.28 (CH$_2$Cl$_2$/MeOH 9/1, v/v). MS m/z 463 (MH$^+$). $^1$H NMR (CDCl$_3$) δ: 2.04 (2H, m), 3.14 (4H, m), 3.34 (2H, m), 3.54 (2H, m), 3.66 (4H, m), 3.86 (5H, m), 4.00 (2H, m), 5.17 (2H, bs), 6.90 (1H, s), 7.18–7.46 (4H, m), 7.53 (2H, m). Found: C,61.90; H,6.34; N,17.29. C$_{25}$H$_{30}$N$_6$O$_3$ 0.1.H$_2$O 0.3.CH$_2$Cl$_2$ requires C,62.04; H,6.34; N,17.16%

EXAMPLE 12

2-Amino-7-methoxy-2-[4-(4-morpholinecarbonyl)-1,4-diazepan-1-yl]-6-(2-pyridinyl)quinazoline The title compound was prepared by the method of Example 11(i) from the compound of Example 1(h), but using (2-pyridinyl)tributylstannane in place of trimethylphenylstannane. MS m/z 464 (MH$^+$).

EXAMPLE 13

2-Amino-7-methoxy-2-[4-(4-morpholinecarbonyl)-1,4-diazepan-1-yl]-6-(3-pyridinyl)quinazoline To a suspension of the compound of Example 11(h) (300 mg, 0.56 mmol) in a mixture of $H_2O$ (1 ml) and THF (6 ml) was added 3-pyridinyldiethylborane (82 mg, 0.56 mmol), tetrakis(triphenylphosphine)palladium (32 mg, 0.028 mmol), tetra-n-butylammonium chloride (15 mg, 0.056 mmol) and KOH (94 mg, 1.68 mmol) and the reaction mixture was heated to reflux for 3 h. After cooling, the reaction mixture was partitioned between EtOAc and $H_2O$, the organic layer separated, dried over $MgSO_4$ and evaporated under reduced pressure. The product was purified by chromatography on silica gel, eluting with $CH_2Cl_2$/MeOH/0.88 $NH_3$ (90/10/1, v/v) followed by recrystallisation from $CH_2Cl_2$/hexane to afford the title compound as a white solid (42 mg, 16%). $R_f$ 0.16 ($CH_2Cl_2$/MeOH/0.88 $NH_3$ 92/7/1, v/v). MS m/z 464 (MH$^+$). $^1$H NMR (CDCl$_3$) δ: 2.05 (2H, m), 3.18 (4H, m), 3.35 (2H, m), 3.56 (2H, m), 3.66 (4H, m), 3.90 (5H, m), 4.03 (2H, m). 5.30 (2H, bs), 6.93 (1H, s), 7.32 (1H, m), 7.43 (1H, s), 7.86 (1H, m), 8.55 (1H, d), 8.73 (1H, s). Found: C,60.14; H,6.17; N,20.14. $C_{24}H_{29}N_7O_3$ 0.9.$H_2O$ requires C,60.09; H,6.47; N,20.44%

EXAMPLE 14

2-Amino-7-methoxy-2-[4-(4-morpholinecarbonyl)-1,4-diazepan-1-yl]-6-(4-pyridinyl)quinazoline To a solution of the compound of Example 11(h) (290 mg, 0.54 mmol) in a mixture of EtOH (6 ml) and toluene (10 ml) was added 4-pyridineboronic acid [Fischer et al Recl. Trav. Chim. Pays Bas, 93, 21 (1974)] (100 mg, 0.81 mmol) tetrakis(triphenylphosphine)palladium (31 mg, 0.027 mmol) and 2N aqueous $Na_2CO_3$ (2 ml) and the mixture was heated to reflux for 3 h. After cooling, the reaction mixture was partitioned between EtOAc and $H_2O$, the organic layer dried over $MgSO_4$ and evaporated under reduced pressure. The residue was purified by chromatography on silica gel, eluting with $CH_2Cl_2$/MeOH/0.88 $NH_3$ (90/10/1, v/v) then triturated sequentially with EtOAc and $CH_2Cl_2$ to afford the title compound as a colourless solid (80 mg, 32%). $R_f$ 0.20 ($CH_2Cl_2$/MeOH/0.88 $NH_3$ 90/10/1, v/v). MS m/z 464 (MH$^+$). $^1$H NMR (CDCl$_3$) δ: 2.02 (2H, m), 3.16 (4H, m), 3.35 (2H, m), 3.54 (2H, m), 3.64 (4H, m), 3.88 (5H, m), 4.00 (2H, m), 5.27 (2H, bs), 6.90 (1H, s), 7.45 (3H, m), 8.65 (2H, m). Found: C,60.78; H,6.22; N,20.24. $C_{24}H_{29}N_7O_3$ 0.7.$H_2O$ requires C, 60.54; H,6.44; N,20.59%

EXAMPLE 15

2-Amino-6-(2-furyl)-7-methoxy-2-[4-(4-morpholinecarbonyl)-1,4-diazepan-1-yl]quinazoline The title compound was prepared by the method of Example 14 from the compound of Example 11(h), but using 2-furanylboronic acid [Florentin et al. J. Heterocyclic Chem., 13, 1265 (1976)] in place of 4-pyridineboronic acid. MS m/z 453 (MH$^+$)

EXAMPLE 16

2-Amino-6-(3-furyl)-7-methoxy-2-[4-(4-morpholinecarbonyl)-1,4-diazepan-1-yl]quinazoline The title compound was prepared by the method of Example 14 from the compound of Example 11(h), but using 3-furanylboronic acid [Florentin et al. J. Heterocyclic Chem., 13, 1265 (1976)] in place of 4-pyridineboronic acid. MS m/z 453 (MH$^+$).

EXAMPLE 17

2-Amino-6-(4-aminosulfonylphenyl)-7-methoxy-2-[4-(4-morpholinecarbonyl)-1,4-diazepan-1-yl]quinazoline (a) (4-Aminosulphonylphenyl)tributylstannane To a solution of p-bromobenzenesulfonamide [Huntress et al. J. Am. Chem. Soc., 62, 511 (1940)] (1.5 g, 6.4 mmol) in toluene (10 ml) was added hexabutylditin (7.3 ml, 19.2 mmol) and tetrakis(triphenylphosphine)palladium (73 mg, 0.063 mmol) and the reaction mixture was heated to 80° C. for 3 h, after which time it was cooled and the resulting suspension passed through a plug of silica gel, washing sequentially with toluene and EtOAc. The EtOAc washings were evaporated under reduced pressure and the residue purified by chromatography on silica gel, eluting with EtOAc/hexane (1/4, v/v) to give the subtitle compound as an oil (1.0 g, 36%). $R_f$ 0.47 (EtOAc/hexane 1/1, v/v).

(b) 2-Amino-6-(4-aminosulfonylphenyl)-7-methoxy-2-[4-(4-morpholinecarbonyl)-1,4-diazepan-1-yl]quinazoline The title compound was prepared by the method of Example 11(i) from the compound of Example 11(h), but using the compound of step (a) in place of trimethylphenylstannane. MS m/z 542 (MH$^+$).

EXAMPLE 18

2-Amino-7-methoxy-2-[4-(4-morpholinecarbonyl)-1,4-diazepan-1-yl]-6-phenylquinoline (a) 5-(Benzyloxy)-4-methoxy-2-{1-[4-(4-morpholinecarbonyl)-1,4-diazepan-1-yl]-ethylideneamino}benzonitrile To a solution of Intermediate 2 (6.02 g, 23.6 mmol) in $CH_2Cl_2$ (100 ml) was added dropwise phosphorus oxychloride (1.31 ml, 12.9 mmol). The mixture was stirred for 20 min at room temperature and then the compound of Example 11(c) (3.0 g, 11.7 mmol) was added and the suspension was heated at reflux for 18 h. After cooling, the reaction mixture was partitioned between $CH_2Cl_2$ (150 ml) and aqueous 1N NaOH (100 ml), the organic phase separated, dried over $MgSO_4$ and evaporated to afford a yellow foam. The product was purified by chromatography on silica gel, eluting with EtOAc/MeOH (97/3, v/v) to afford the subtitle compound as a pale yellow glass (3.35 g, 58%). $R_f$ 0.54 ($CH_2Cl_2$/MeOH 9/1, v/v). MS m/z 492 (MH$^-$).

(b) 5-Hydroxy-4-methoxy-2-{1-[4-(4-morpholinecarbonyl)-1,4-diazepan-1-yl]-ethylideneamino}benzonitrile The subtitle compound was prepared by the method of Example 11(g) from the product of step (a). This afforded the subtitle compound (90%) as a colourless solid. $R_f$ 0.47 ($CH_2Cl_2$/MeOH 9/1, v/v).

(c) 4-Methoxy-2-{1-[4-(4-morpholinecarbonyl)-1,4-diazepan-1-yl]ethylideneamino}-5-(trifluoromethanesulfonato)benzonitrile The subtitle compound was prepared by the method of Example 11(h) from the product of step (b). This afforded the subtitle compound (54%). $R_f$ 0.70 ($CH_2Cl_2$/MeOH 9/1, v/v)

(d) 4-Methoxy-2-{1-[4-(4-morpholinecarbonyl)-1,4-diazepan-1-yl]ethylideneamino}-5-phenylbenzonitrile The subtitle compound was prepared by the method of Example 14 from the product of step (c) using phenylboronic acid. This afforded the subtitle compound as a colourless solid (75%). $R_f$ 0.34 ($CH_2Cl_2$/MeOH 95/5, v/v). MS m/z 461 ($MH^+$).

(e) 2-Amino-7-methoxy-2-[4-(4-morpholinecarbonyl)-1,4-diazpan-1-yl]-6-phenylquinoline To a solution of the product of step (e) (315 mg, 0.68 mmol) in THF (10 ml) at −20° C. was added a solution of lithium diisopropylamide in THF (0.68M, 2 ml, 1.36 mmol) and the reaction allowed to warm to room temperature. The reaction mixture was poured into cooled 1N citric acid, the solution basified with $Na_2CO_3$ and extracted with EtOAc. The organic layer was dried over $MgSO_4$ and evaporated to afford a residue that was purified by chromatography on silica gel, eluting with $CH_2Cl_2$/MeOH/$NH_3$ (90/10/1, v/v) followed by trituration with EtOAc to afford the title compound as an off-white solid (109 mg, 35%). $R_f$ 0.46 ($CH_2Cl_2$/MeOH/0.88 $NH_3$ 90/10/1, v/v). MS m/z 462 ($MH^-$). $^1H$ NMR ($CDCl_3$) δ: 2.08 (2H, m), 3.12 (4H, m), 3.37 (2H, m), 3.64 (6H, m), 3.75 (2H, m), 3.90 (3H, s), 4.02 (2H, m), 4.41 (2H, bs), 5.96 (1H, s), 7.07 (1H, bs), 7.37 (1H, m), 7.46 (3H, m), 7.58 (2H, m). Found: C,65.28; H,6.89; N,14.15. $C_{26}H_{31}N_5O_3$ $H_2O$ 0.1.EtOAc requires C,64.93; H,6.98; N,14.34%

EXAMPLE 19

2-Amino-7-methoxy-2-[4-(4-morpholinecarbonyl)-1,4-diazepan-1-yl]-6-(2-pyridinyl)quinoline (a) 4-Methoxy-2-{1-[4-(4-morpholinecarbonyl)-1,4-diazepan-1-yl]ethylideneamino}-5-(2-pyridinyl)benzonitrile The subtitle compound was prepared by the method of Example 11(i) from the compound of Example 18(c) and (2-pyridinyl)tri-n-butylstannane.

(b) 2-Amino-7-methoxy-2-[4-(4-morpholinecarbonyl)-1,4-diazepan-1-yl]-6-(2-pyridinyl)quinoline The title compound was prepared by the method of Example 18(e) from the compound of step (a). MS m/z 463 ($MH^+$).

EXAMPLE 20

4-Amino-7-methoxy-2-(5-methanesulfonamido-1,2,3,4-tetrahydroisoquinol-2-yl)-6-(2-pyridinyl)quinoline (a) 4-Methoxy-2-nitro-5-(2-pyridinyl)benzoic acid, methyl ester The subtitle compound was prepared from the compound of Example 1(b) by the method of Example 11(i) using (2-pyridinyl)tri-n-butylstannane. The product was purified by chromatography on silica gel, eluting with $CH_2Cl_2$/MeOH (99:1) followed by trituration with ether to afford the subtitle compound (39%) as a colourless solid. $R_f$ 0.64 ($CH_2Cl_2$/MeOH/95/5, v/v). MS m/z 289 ($MH^-$).

(b) 4-Methoxy-2-nitro-5-(2-pyridinyl)benzamide

To a suspension of the product of step (a) (3.30 g, 11.5 mmol) in MeOH (100 ml) was added 2N aqueous NaOH (6.3 ml, 12.6 mmol) and the reaction mixture was stirred for 64 h at room temperature followed by heating to reflux for 6 h. After cooling, the reaction mixture was concentrated under reduced pressure, the residue suspended in $CH_2Cl_2$ (100 ml) and DMF (0.5 ml) was added. Oxalyl chloride (3.06 ml, 34.4 mmol) was then added and the mixture was stirred rapidly at room temperature for 4 h then evaporated under reduced pressure. The residue was suspended in $CH_2Cl_2$ and poured into a rapidly stirred solution of 0.88 aqueous $NH_3$. The resulting mixture was stirred for 15 min and the solid formed was isolated by filtration, washing with $CH_2Cl_2$ and $H_2O$. The solid was dried under vacuum at 65° C. for 18 h to afford the subtitle compound as a colourless solid (2.50 g, 80%). $R_f$ 0.27 (EtOAc). MS m/z 274 ($MH^+$).

(c) 4-Methoxy-2-nitro-5-(2-pyridinyl)benzonitrile

A solution of the product of step (b) (2.40 g, 8.8 mmol) in $CH_2Cl_2$ was treated with trifluoroacetic anhydride (20 ml) and the reaction mixture stirred for 2 h at room temperature and at reflux for a further 1 h. After cooling, the reaction mixture was evaporated under reduced pressure, the residue basified with 1N aqueous NaOH and extracted with $CH_2Cl_2$ (3×). The combined organic extracts were dried over $MgSO_4$ and evaporated under reduced pressure. The residue was purified by chromatography on silica gel, eluting with EtOAc to afford the subtitle compound (1.73 g, 77%). $R_f$ 0.58 (EtOAc). MS m/z 256 ($MH^+$).

(d) 2-Amino-4-methoxy-5-(2-pyridinyl)benzonitrile

The subtitle compound was prepared by the method of Example 1(d) from the product of step (c). The product was purified by chromatography on silica gel, eluting with EtOAc to afford the subtitle compound (69%) as a yellow solid. $R_f$ 0.46 (EtOAc). MS m/z 226 ($M^+$).

(e) 2-[1-(5-Methanesulfonamido-1,2,3,4-tetrahydroisoquinol-2-yl)ethylideneamino]-4-methoxy-5-(2-pyridinyl)benzonitrile The subtitle compound was prepared by the method of Example 18(a) from the product of step (d) and Intermediate 4. The product was purified by chromatography on silica gel, eluting with EtOAc, followed by trituration with ether to afford the subtitle compound (61%) as a pale yellow solid. $R_f$ 0.35 (EtOAc). MS m/z 476 ($MH^-$).

(f) 4-Amino-7-methoxy-2-(5-methanesulfonamido-1,2,3,4-tetrahydroisoquinol-2-yl)-6-(2-pyridinyl)quinoline To a solution of the product of step (e) (961 mg, 2.0 mmol) in DMSO (12 ml) was added KOH (226 mg, 4.0 mmol) and the mixture was heated to 95° C. under $N_2$ for 20 min. After cooling, the reaction was quenched with saturated aqueous ammonium chloride and extracted with EtOAc. The organic layer was washed sequentially with $H_2O$ and saturated brine then dried over $MgSO_4$ and evaporated under reduced pressure. The residue was purified by chromatography on silica gel, eluting with $CH_2Cl_2$/MeOH/0.88 $NH_3$ (92/7/1, v/v) followed by trituration with ether to afford the title compound as a colourless solid (656 mg, 69%). $R_f$ 0.14 ($CH_2Cl_2$/MeOH/0.88 $NH_3$ 92/7/1, v/v). MS m/z 476 ($MH^+$). $^1H$ NMR ($CDCl_3$) δ: 2.82 (2H, m), 2.99 (3H, s), 3.88 (2H, m), 3.93 (3H, s), 4.64 (2H, bs), 4.82 (2H, s), 6.58 (1H, bs), 7.05–7.15 (6H, m), 7.67 (1H, t), 7.88 (1H, d), 8.07 (1H, s), 8.63 (1H, d). Found: C,59.84; H,5.38; N,13.51. $C_{25}H_{25}N_5O_3S$ 1.5. $H_2O$ requires C,59.75; H,5.62; N,13.93%

EXAMPLE 21

The compound of Example 11 was tested in the first screen described above ("Contractile responses of human prostate") and found to have a $pA_2$ value of 8.7.

What is claimed is:

1. A compound of formula I,

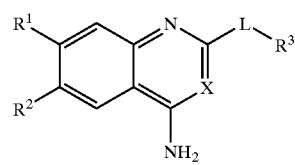

wherein
  $R^1$ represents $C_{1-4}$ alkoxy optionally substituted by one or more fluorine atoms;

$R^2$ represents an aryl group selected from phenyl or naphthyl or a heteroaryl group selected from pyridinyl or furanyl, each aryl or heteroaryl group optionally substituted by $C_{1-4}$ alkyl or $SO_2NH_2$;

$R^3$ represents a heterocyclic ring selected from morpholine, thiomorpholine-1,1-dioxide, 1,4-dioxan, tetrahydrofuran, piperidine, optionally fused to a benzene or pyridine ring, or 1,4-benzodioxane, each ring system as a whole being optionally substituted by one or more groups independently selected from OH, $C_{1-4}$ alkyl, $C_{1-4}$ alkoxy, halogen and $NHSO_2(C_{1-4}$ alkyl);

X represents N; and

L is absent, or represents a cyclic group of formula Ia,

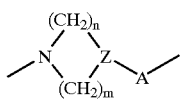

Ia in which A is attached to $R^3$;

A represents CO or $SO_2$;

Z represents CH or N;

m represents 1 or 2, and in addition, when Z represents CH, it may represent 0; and n represents 1, 2 or 3, provided that the sum of m and n is 2,3,4 or 5; or represents a chain of formula Ib,

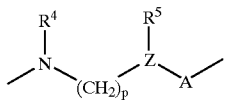

Ib in which A is attached to R-hu 2;

A and Z are as defined above;

$R^4$ and $R^5$ independently represent H or $C_{1-4}$ alkyl; and p represents 1, 2 or 3, and in addition, when Z represents CH, it may represent 0; or a pharmaceutically acceptable salt thereof.

2. A compound as claimed in claim 1, wherein $R^1$ represents methoxy.

3. A compound as claimed in claim 1, wherein $R^2$ represents phenyl or 2-pyridinyl.

4. A compound as claimed in claim 1, wherein $R^3$ represents morpholinyl, or a piperidine ring which is fused to a benzene or pyridine ring.

5. A compound as claimed in claim 1, wherein L is absent or represents

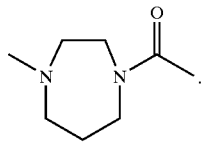

6. A compound as claimed in claim 1, wherein L is absent and $R^3$ represents a piperidine ring fused to a benzene ring which is substituted by $NHSO_2(C_{1-4})$alkyl.

7. A pharmaceutical formulation comprising a compound of formula I, as defined in claim 1, or a pharmaceutically acceptable salt thereof, in admixture with a pharmaceutically acceptable adjuvant, diluent or carrier.

8. A method of treating benign prostatic hyperplasia which method comprises administering an effective amount of a compound of formula I, as defined in claim 1, or a pharmaceutically acceptable salt thereof, to a patient in need of such treatment.

* * * * *